(12) United States Patent
Kuiper et al.

(10) Patent No.: US 11,304,796 B2
(45) Date of Patent: Apr. 19, 2022

(54) REINFORCEMENT RING FOR INTRAOCULAR LENS

(71) Applicant: Verily Life Sciences LLC, Mountain View, CA (US)

(72) Inventors: Stein Kuiper, Pacifica, CA (US); Daniel B. Otts, Pleasanton, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 537 days.

(21) Appl. No.: 16/134,776

(22) Filed: Sep. 18, 2018

(65) Prior Publication Data
US 2019/0091011 A1    Mar. 28, 2019

Related U.S. Application Data

(60) Provisional application No. 62/562,631, filed on Sep. 25, 2017.

(51) Int. Cl.
*A61F 2/16*      (2006.01)
*G02C 7/08*     (2006.01)
(Continued)

(52) U.S. Cl.
CPC .......... *A61F 2/1624* (2013.01); *A61F 2/1635* (2013.01); *A61F 2/482* (2021.08); *A61F 2210/0014* (2013.01); *A61F 2250/0002* (2013.01); *G02C 7/04* (2013.01); *G02C 7/085* (2013.01)

(58) Field of Classification Search
CPC .................. A61F 2/1624; A61F 2/1635; A61F 2002/482; A61F 2210/0014; A61F 2250/0002; G02C 7/04; G02C 7/085
See application file for complete search history.

(56) References Cited

U.S. PATENT DOCUMENTS 4,418,991 A    12/1983  Breger
4,878,910 A *  11/1989  Koziol ................. A61F 2/1613
                                                               623/6.38

(Continued)

FOREIGN PATENT DOCUMENTS

EP        1798578 A1    6/2007
WO       8701931 A1    4/1987
(Continued)

OTHER PUBLICATIONS

International Search Report and Written Opinion dated Jan. 2, 2019 for corresponding International Patent Application No. PCT/US2018/052061, 13 pages.

(Continued)

*Primary Examiner* — Thomas C Barrett
*Assistant Examiner* — Tiffany P Shipmon
(74) *Attorney, Agent, or Firm* — Christensen O'Connor Johnson Kindness PLLC

(57) ABSTRACT

An example reinforcement ring for intraocular lenses may include at least include a support structure, first and second optical windows disposed on opposing sides of the support structure, and a reinforcement ring included in the apparatus to strengthen the support structure and the first and second optical windows. In some examples, the reinforcement ring is formed from a shape memory alloy, such as Nitinol.

25 Claims, 4 Drawing Sheets

(51) Int. Cl.
 *G02C 7/04* (2006.01)
 *A61F 2/48* (2006.01)

(56) References Cited

U.S. PATENT DOCUMENTS

| | | | |
|---|---|---|---|
| 5,180,390 A | 1/1993 | Drews | |
| 7,553,019 B2 | 6/2009 | Kuiper et al. | |
| 8,048,156 B2* | 11/2011 | Geraghty | A61F 2/1624 623/6.37 |
| 8,215,770 B2 | 7/2012 | Blum et al. | |
| 2006/0095128 A1* | 5/2006 | Blum | G02C 7/083 623/6.37 |
| 2012/0078363 A1* | 3/2012 | Lu | A61F 2/1635 623/6.37 |
| 2012/0140167 A1* | 6/2012 | Blum | G02C 7/04 351/159.34 |
| 2013/0184815 A1 | 7/2013 | Roholt | |
| 2014/0002789 A1 | 1/2014 | Pugh et al. | |
| 2016/0166432 A1 | 6/2016 | Kahook et al. | |
| 2016/0220354 A1 | 8/2016 | Lee | |
| 2016/0220355 A1 | 8/2016 | Lee | |
| 2016/0235524 A1* | 8/2016 | Wortz | A61F 2/16 |
| 2016/0331521 A1 | 11/2016 | Deboer et al. | |

FOREIGN PATENT DOCUMENTS

| | | |
|---|---|---|
| WO | 9527912 A1 | 10/1995 |
| WO | 2016/160456 A1 | 10/2016 |

OTHER PUBLICATIONS

Chinese Office Action dated Jun. 18, 2021, in corresponding Chinese Patent Application No. 201880062243.4, 13 pages.
Chinese Office Action dated Feb. 22, 2022, in corresponding Chinese Patent Application No. 201880062243.4, 9 pages.

* cited by examiner

REINFORCEMENT RING FOR INTRAOCULAR LENS

CROSS-REFERENCE TO RELATED APPLICATION

This application claims the benefit of U.S. Provisional Application No. 62/562,631, filed Sep. 25, 2017, which is hereby incorporated by reference in its entirety.

TECHNICAL FIELD

This disclosure relates generally to ophthalmic devices, and in particular but not exclusively, relates to ophthalmic devices that include a reinforcement ring.

BACKGROUND INFORMATION

Presbyopia treatment may include implantation of a replacement lens. Such lenses, which may also be referred to as intraocular lenses, may provide static or dynamic accommodation, or a combination thereof. Various techniques may be available to provide dynamic accommodation, such as mechanical or electrical controlled accommodation. The accommodation may be provided by actuation of a dynamic optical component that provides multiple levels of optical power. The change in optical power may provide different focal distances to the user via the intraocular lens. The amount of actuation, however, may depend on the technique used, e.g., mechanical or electrical.

The implantation of these types of lenses conventionally uses a small incision where the lens is rolled or folded so it fits through the small incision. This method may be preferable to physicians to limit the size of the cut in the eye. While rolling and folding soft materials may be possible, intraocular lenses that include electrical parts and other internal components may be formed from multiple pieces that are assembled to form the lens. Some of these pieces, however, may warp upon unfolding, which can cause poor optical quality. As such, it is desirable to ensure that intraocular lenses fully straighten upon unfolding to reduce warping.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
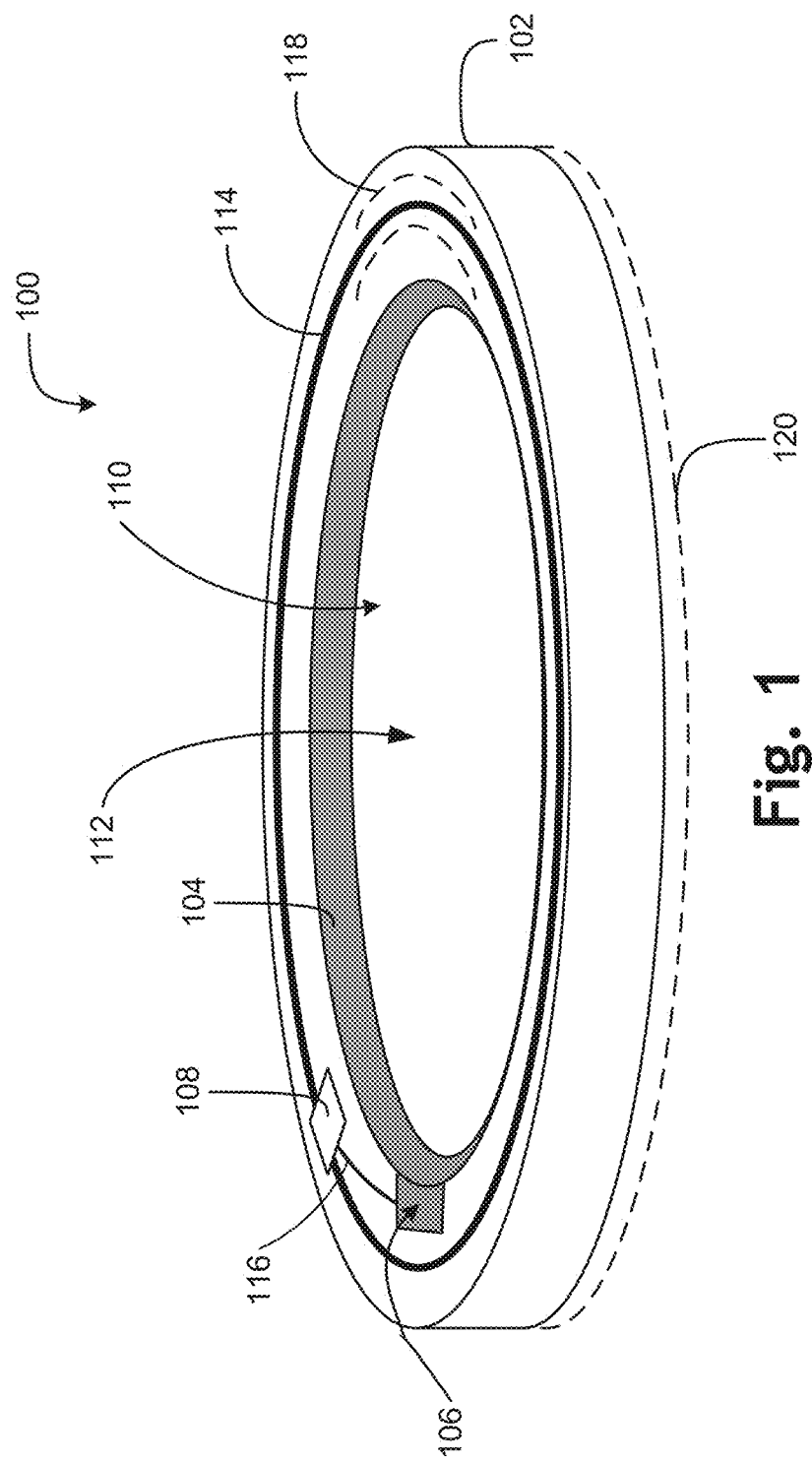
FIG. 1 is a perspective view of an intraocular lens (IOL) including one or more reinforcement rings in accordance with an embodiment of the disclosure.

Embodiments of an apparatus and method for an intraocular lens having a reinforcement ring are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An IOL may be implanted in a user's eye to assist in accommodation when the user's lens is no longer able to change focus, for one example. The IOL may have static optical power or may have the ability to dynamically accommodate, e.g., alter the optical power of the IOL, so the user may change focus similar to the natural eye. To provide dynamic accommodation, the IOL may include electronics, conductive traces, electrodes, and the like, coupled to a dynamic optic located in an optical path of the IOL. The electronics may provide a voltage to the dynamic optic via one or more conductors to cause accommodation, for example. Additionally, the electronics may be enclosed in one or more soft components, which may form a support structure, and optical windows.

Additionally, because the IOL will be implanted into the eye, a small incision in the eye may be desirable. Yet, because the IOL may be of the same size as the original lens, for example, a large incision may be required. However, if the IOL is capable of being rolled up into a cylindrical shape or folded, a smaller incision may be possible. In general, most of the materials forming the IOL are amenable to being rolled or folded, but various components of the IOL may become warped, which may reduce optical quality. For example, the optical windows of the IOL may become warped from rolling and unrolling, and/or from prior fabrication steps, where the warpage may negatively impact the optical quality of the IOL. Accordingly, it may be desirable for the IOL to include strong, flexible and stretchable components that may provide some stiffness to the IOL once it has been unfolded/unrolled. For example, a reinforcement ring that is strong, flexible and deformable, e.g., elastic, may be incorporated into the IOL. The reinforcement ring, which may be flexible enough to withstand the folding/rolling, may return a desired shape upon unrolling/unfolding without experiencing inelastic deformation. Further, the reinforcement ring may cause the IOL to become taut and stretched due to being stronger than the surrounding soft components. For example, the reinforcement ring may be insert-molded in silicone resin and cured at an elevated temperature. Upon cooling down, the silicone shrinks more than the reinforcement ring, thus leaving the silicone under tensile stress, which will stretch the silicone and thus prevent it from warping. The achieved taut condition may subsequently reduce or eliminate the warpage in the optical windows.

It should be noted that while this discussion is centered on IOLs, such discussion is not intended to be limiting, and all aspects of the disclosure are equally applicable to on-eye wearable ophthalmic devices, to give at least one example.

In general, the features of the disclosure are directed toward reinforcement rings for devices that may experience bending and/or rolling, and that may assist in a return to a desired shape upon unrolling/bending.

FIG. 1 is a perspective view of an IOL 100 including one or more reinforcement rings in accordance with an embodiment of the disclosure. The illustrative embodiment of the IOL 100 includes a support structure 102, an electrode 104, a contact pad 106, control electronics 108, a dynamic optic 112, an antenna 114, a conductor 116, a reinforcement ring 118, and an optical window 120. An additional optical window may also be included but is not shown in FIG. 1 (see FIG. 2 for an example). While not shown, the IOL 100 may be enclosed in a transparent or semitransparent biocompatible material. As noted above, the IOL 100 may be rolled up and/or folded for insertion into a user's eye, and the IOL 100 may desirably return to a straight and stretched, e.g., taut, state after unrolling/unfolding. To ensure that the taut state is achieved, one or more reinforcement rings may be included in the IOL 100 that provide the strength for obtaining the desired taut state. The one or more reinforcement rings may stretch the support structure 102 and the optical windows so that no or little warpage is present.

The support structure 102 may provide mechanical support for the various features of the IOL 100. For example, the support structure 102 may provide support for the electrode 104, the contact 106, the control electronics 108, the dynamic optic 112, the optical window 120, the conductor 116, the antenna 114, the reinforcement ring 118, and various other components discussed herein. In some embodiments, however, some of the components, such as the control electronics, 108, the conductor 116, the antenna 114, and the contact 106 may be disposed on a separate substrate (not shown), which may then be disposed on a surface of the support structure 102 or embedded within the support structure 102. In some embodiments, the reinforcement ring 118, which is included with the support structure 102, provides the substrate for mounting of the various electronic components. Of course, other arrangements are possible and the reinforcement ring 118 may not function as a substrate for the electronic components.

In general, the support structure 102 may be formed from a biocompatible material that is amenable to implantation into an eye. Example materials may include silicones, sol-gels, and AcrySof®. Other biocompatible materials, such as biocompatible hydrogel, hydrophobic acrylic, fluorinated polymethacrylate and/or the like, may also be used. The support structure 102 may be a main structural component of the IOL 100 that provides a platform for other IOL 100 components. The support structure 102 may be flexibly capable of being rolled up and/or folded so that it may be manipulated into a smaller shape to accommodate insertion into an eye through a small incision, e.g., an incision roughly 2 mm in length. The support structure 102 is preferably highly elastic, so that it will return to its original shape after unrolling/unfolding. In some embodiments, the support structure 102 can be annulus-shaped, e.g., washer-shaped, having an opening 110, e.g., an aperture, formed there through. The opening 110 may provide an optical path for the IOL 100. In such embodiments, the optical window 120 is placed over at least the opening 110 on one side of the support structure 102, and a second optical window may be disposed over the opening 110 on the other side of the support structure 102.

The opening 110 may be formed by an inner surface, e.g., a sidewall, of the support structure 102. In some embodiments, the sidewall may be at a non-orthogonal angle, e.g., an oblique angle, to top and/or bottom surfaces, e.g., surfaces 224 and 226, of the support structure 102. For example, the sidewall may be at a 45° angle to at least one of the top or bottom surfaces of the support structure 102. In general, the type of dynamic optic 112 of the IOL 100 may determine a slope or angle of the sidewall with respect to a top or bottom surfaces of the support structure 102, and other angles other than 45° are within the scope of the present disclosure. For example, an electrowetting-based dynamic optic, such as the illustrated dynamic optic 112, the sidewall may be at an oblique angle, and may be in the shape of a conical frustum in some embodiments. However, if the dynamic optic is based on liquid crystal technology, then the angle of the sidewall may be orthogonal to the top and bottom surfaces of the support structure 102.

In the illustrated embodiment, the electrode 104 may be disposed on the sidewall, and may generally conform to the shape of the sidewall. For example, if the sidewall is shaped as a conical frustum, then the electrode 104 may similarly shaped. In some embodiments, the electrode 104 may have one or more dielectric layers disposed over that assist with implementing the electrowetting technology. For example, charge provided to the electrode, which may form a potential difference with a a polar liquid of the dynamic optic 112, may alter the surface energy of the overlying dielectric. The altered surface energy, in turn, may cause a meniscal interface to move up or down the electrode, which provides lensing to the IOL 100. In general, the electrode 104 may be formed from a flexible, conductive material that is amenable to being rolled and unrolled without experiencing inelastic deformation. For example, the electrode 104 may be formed from a superelastic alloy, shape memory alloy, a flexible alloy mesh, or the like.

The contact pad 106 may electrically couple the control electronics 108 to the dynamic optic 112, and may be disposed on a surface of the support structure 102, or a substrate embedded in the support structure. In some embodiments, the contact pad 106 may be part of the electrode 104. However, the contract pad 106 does not need to be part of the electrode, and may be a separate component. Additionally, the contact pad 106 may be coupled to the control electronics via one or more conductors 116. The control electronics 108 may be coupled to at least provide a voltage to the dynamic optic 112. In the illustrated embodiment, the control electronics 108 are coupled to the dynamic optic 112 via the conductor 116, the contact pad 106 and the electrode 104.

The antenna 114 may be formed into a loop around the aperture 110, and may be coupled to the control electronics 108. The antenna 114 may allow for wireless communication between the IOL 100 and an external reader, for example, and in some embodiments may also allow for wireless charging of onboard power sources. In some embodiments, the antenna 114 may be formed from a superelastic metal alloy, and may provide reinforcement ring aspects to the IOL 100. For example, an antenna 114 formed from a superelastic alloy may add the desired strength to the IOL 100 to reduce or prevent the optical windows from being warped after unrolling/unfolding of the IOL upon implantation.

The reinforcement ring 118 may be formed into an annular shape and sized to encompass the aperture 110. In some embodiments, the reinforcement ring may have an inner diameter of 6 mm, an outer diameter of 7 mm, and a thickness of 100 to 200 microns, but of course other dimensions are possible. The reinforcement ring 118 may further be sized to fit on a top or bottom surface of the support structure 102, or fit within the support structure 102. For example, the reinforcement ring 118 may be embedded in the support structure 102. It may be desirable that the reinforcement ring 118 is formed from a strong yet flexible material that can withstand being folded/rolled to a radius of around 1 mm, but return to a desired shape upon unfolding/unrolling. Additionally, the reinforcement ring 118 may desirably be strong enough to force the soft components of the IOL 100, such as the support structure 102 and the optical windows, into a desired tautness and straightness to achieve a desired optical quality.

To that end, the reinforcement ring 118 may be formed from an elastic, superelastic, or pseudoelastic metal alloy. In some embodiments, the reinforcement ring 118 may be formed from spring steel, or a shape-memory alloy. For example, the shape-memory alloy may be Nitinol (nickel-titanium alloy) of various compositions, copper-zinc-aluminum, copper-aluminum, copper-aluminum-nickel, or copper-aluminum-beryllium. In some embodiments, the Nitinol may be in an annealed, shape set form, which allows it to fold back completely after unfolding. Alternatively, the Nitinol may be in a body temperature shape memory alloy composition that allows it to be folded at room temperature and kept in that shape until it is inserted into the eye where it unfolds due to the surrounding body temperature. In other embodiments, it may be desirable to form the reinforcement ring 118 out of a biocompatible elastic metal alloy, such as medical grade titanium having high elasticity. For example, the medical grade titanium may be Ti6Al4V. In yet other embodiments, the reinforcement ring 118 may be formed from stiff elastic polymers, such as polyimide or polyetherimide. Other plastics may be used to form the reinforcement ring 118, such as polyethelyne terephthalate (PET), polyether ether ketone (PEEK), and blends or copolymers thereof.

The IOL 100 may include one or more reinforcement rings 118, which may be included in various locations. For example, the reinforcement ring 118 may be embedded in the support structure 102, under the electrode 104, within one or both optical windows, and the like. In some embodiments, a reinforcement ring 118 in the support structure 102 may be coupled to a reinforcement ring 118 in one of the optical windows. In such an embodiment, the clamping of the two reinforcement rings 118 may assist with assembling the IOL 100 and attaching the optical window to the support structure 102. In general, the reinforcement ring 118 may be much stiffer than the soft components, such as the support structure 102 and the optical window 120, and forces the soft components into a well-defined straight position upon unfolding/unrolling of the IOL 100.

Figure 2:
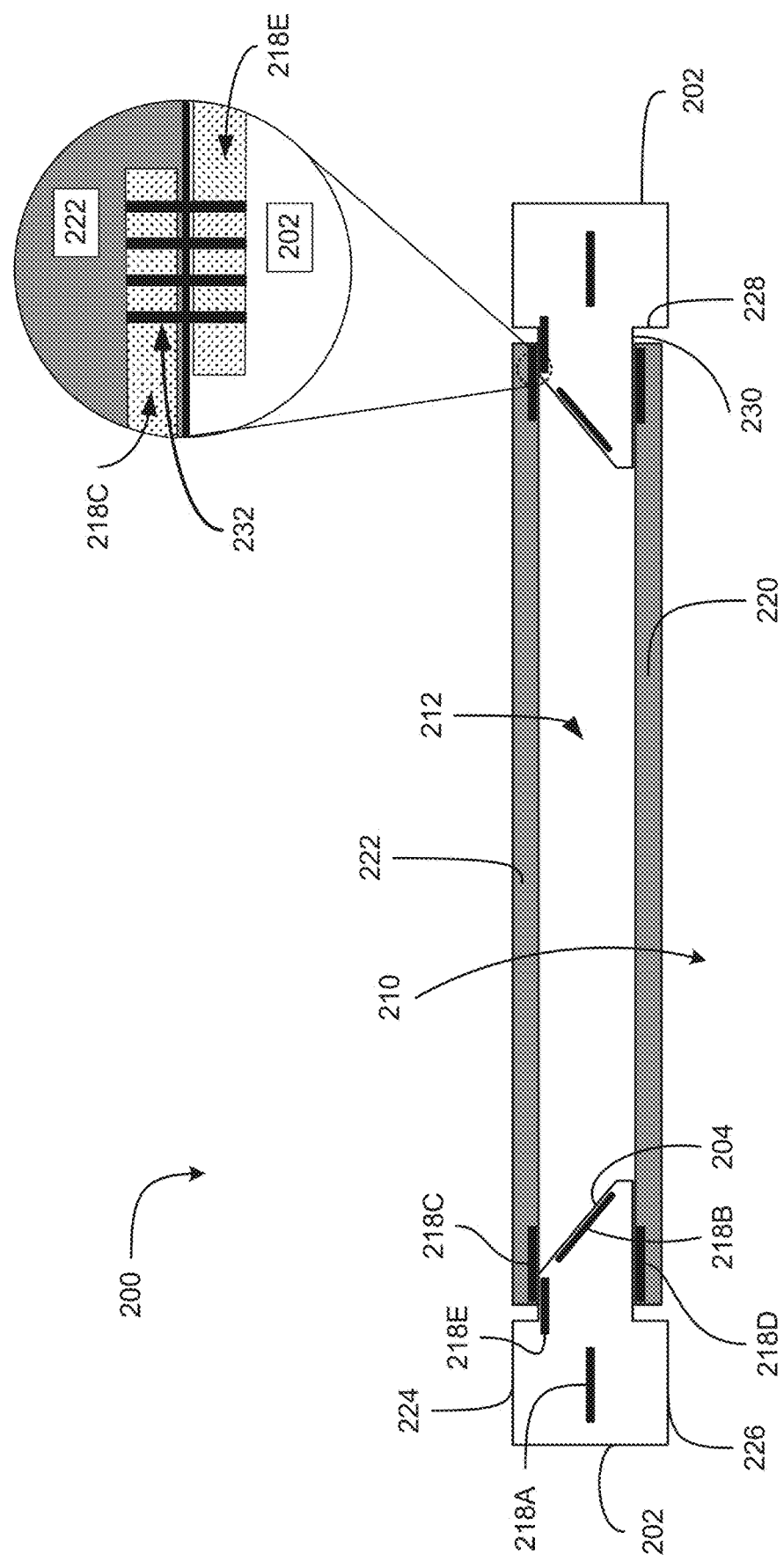
FIG. 2 is a cross-sectional illustration of a portion of an IOL including one or more reinforcement rings in accordance with an embodiment of the present disclosure.

FIG. 2 is a cross-sectional illustration of a portion of an IOL 200 including one or more reinforcement rings in accordance with an embodiment of the present disclosure. The IOL 200 may be an example of the IOL 100. The IOL 200 at least includes a support structure 202, an electrode 204, a dynamic optic 212, optical windows 220 and 222, and one or more reinforcement rings 218, such as reinforcement rings 218A through 218E. The IOL 200 shows the various locations for positioning the reinforcement ring 218, and more than one reinforcement ring 218 may be included in an IOL 200. The reinforcement ring 218 may stretch and straighten the IOL 200 when in an unfolded state (as shown), which may ensure there is no or minimal warping of the support structure 202 and/or the optical windows 220, 222. Warpage of the IOL 200, such as in the optical windows 220, 222, may reduce the optical quality of the IOL 200.

The support structure 202 provides mechanical support for the various other components of the IOL 200. Similar to the support structure 102, the support structure 202 may be formed into an annular shape and may be composed of a biocompatible, soft material. The support structure 202 is amenable to being folded/rolled and unfolded/unrolled without experiencing any damage. The support structure 202 may be molded from a desired material, such as silicones, sol-gels, and AcrySof®. and the various other components, such as the electronics and the reinforcement ring 218, may be embedded within the support structure 202. The electronics in the IOL 200 refer to control electronics, conductors, contact pads, an antenna, and the electrode 204.

The support structure 202 may further have a recess formed on an inner edge on both the top and bottom surfaces 224, 226 that encircles the aperture 210. The recesses may provide a surface for mounting and sealing the optical windows 220, 222 to the support structure 102. The recess may be defined by surfaces 228 and 230 formed into the bottom surface 226, which may be mirrored on the top surface 224. In some embodiments, the recess formed into the top surface 224 and the recess formed into the bottom surface 226 may be different and provide different surface areas of the support structure 202. Of course, the support structure 202 may be formed without the surfaces 228 and 230 and the optical windows 220 and 222 may, instead, be disposed on the top and bottom surfaces 1224 and 226, respectively.

The electrode 204 may be disposed on an inner sidewall of the support structure 202. The electrode 204 may be formed from a flexible conductor, and may be formed from a superelastic alloy in some embodiments. The electrode 204 may be coupled to control electronics and provided a voltage to adjust the dynamic optic 212.

The dynamic optic 212 may be arranged in an aperture 210 of the support structure 202, and may be coupled to control electronics via the electrode 204. In some embodiments, the dynamic optic 212 may be based on electrowetting technology, which includes two immiscible fluids (one fluid being a polar fluid) enclosed in the aperture 210 and the optical windows 220 and 222. By changing a potential difference between the electrode 204 and the polar fluid, the interface may move up and down the electrode 204, thereby changing an optical power of the dynamic optic 212. The polar fluid is coupled to receive a voltage from the control electronics 108, for example.

The optical windows 220, 222 may be mounted to top and bottom sides of the support structure 202. The first and second optical windows 220, 222 may be formed from transparent or partially transparent polymerics or thin glass. Example polymerics include Polydimethylsiloxane, hydrophobic acrylic (e.g., AcrySof®), of silicones, acrylics, epoxies, urethanes, combinations thereof, and the like. While top and bottom are used herein to discuss the opposite sides of the support structure 202, the top and bottom designations do not notate any directionality to the IOL 200 and are used merely as a reference with respect FIG. 2.

The optical windows 220, 222 may be transparent and disposed to cover the aperture 210. The optical windows 220, 222 may be with or without optical power. In some embodiments, one or both of the optical windows provides static optical power to the IOL 200, which may be affected by the dynamic accommodation of the IOL 200. In some embodiments, the optical windows 220, 222 do not have any optical power. In either embodiment, the optical windows 220, 222 may be coupled to the support structure 102 to retain the two immiscible fluids within the cavity formed by the support structure 202 and the optical windows 220, 222.

Additionally, one or both of the optical windows may be conductive. For example, the optical window 220 and/or 222 may be conductive. A transparent conductor, such as indium tin oxide (ITO) may be deposited on the optical windows 118 and/or 120, for example. Having one or both of the optical windows conductive may allow a potential difference to be applied to the dynamic optic 112 for causing changes in accommodation.

Further, during assembly of the IOL 200, one or both of the optical windows 220, 222 may be sealed to the support structure 202. During this process, however, there is a chance that one or both of the optical windows 220, 222 may be warped. Such warpage may unfortunately reduce the optical quality of the IOL 200. To counteract any such warpage, one or more reinforcement rings 218 are included in the IOL 200. The one or more reinforcement rings 218 may be strong enough to stretch and straighten the support structure 202 and/or optical windows 220, 222 after unfolding/unrolling for the IOL 200 to remove or reduce any incidence of warpage.

As noted above, the reinforcement ring 218 may be formed from a superelastic alloy. Depending on the superelastic alloy implemented, the reinforcement ring 218 may be of varying thicknesses. For example, if the reinforcement ring is formed from a shape memory alloy, such as Nitinol, the reinforcement ring 218 may be from 100 to 200 microns in thickness. Such thickness may provide the strength to ensure the IOL 200 is stretched and straightened after unrolling/unfolding to mitigate any warpage present in the optical windows and/or the support structure. Of course, other superelastic alloys at different thicknesses are also possible.

In general, a reinforcement ring 218 may be embedded in the support structure 202, one or both of the optical windows 220, 222, or a combination thereof. The various reinforcement rings 218 shown in FIG. 2 are included to illustrate the various locations a reinforcement ring may be disposed. In some embodiments, only one reinforcement ring 218 may be included, but other embodiments may have two or more reinforcement rings 218.

A reinforcement ring 218A may be embedded in a main portion of the support structure 202. The reinforcement ring 218A may be larger than the aperture 210 and encompass the aperture 210. In some embodiments, the reinforcement ring 218A may also be a substrate for the various electronics of the IOL 200, such as the control electronics, the antenna, and such. In other embodiments, the reinforcement ring 218A may not double as a substrate. Alternatively, the reinforcement ring 218A may double as the antenna, such as the antenna 114, or a conductor in contact with the polar fluid of the dynamic optic.

A reinforcement ring 218B may be embedded adjacent to the sidewall of the support structure 202 and underneath the electrode 204. In such an arrangement, the reinforcement ring 218 may be formed to conform to a shape of the sidewall. For example, the reinforcement ring 218B may be formed into a conical frustum shape to conform to the sidewall. However, other shapes are also contemplated, and may be based on the specific design of the support structure 202. Alternatively, the reinforcement ring 218B may be implemented as the electrode 204 in some embodiments.

The reinforcement rings 218C and 218D may be respectively embedded in optical windows 220, 222. The IOL 200 may include one or both of the reinforcement rings 218C and 218D. Additionally, embedding the reinforcement rings 218C, D into their respective optical windows may ease handling of the optical windows during assembly of the IOL 200. Further, because the reinforcement rings 218C, D may stretch their respective optical windows before assembly, the stiffness added to the optical windows due to the reinforcement rings 218C, D may reduce the incidence of warpage during assembly.

The reinforcement ring 218E may be disposed in the support structure 202 in an area adjacent to where the optical window 220 is attached to the support structure 202. For example, the reinforcement ring 218E may be disposed under the recess surface 230 formed on the top surface 224. While not shown in FIG. 2, a second reinforcement ring 218E may be disposed adjacent to the optical window 222 as well. By disposing the reinforcement ring 218E adjacent to the optical window 220, the strength of the reinforcement ring 218E may be more directly translated to the optical window 220, thereby stretching the optical window 220 more directly than the reinforcement ring 218A.

In some embodiments, the reinforcement ring 218C and 218E may both be included in the IOL 200, and they may be coupled together (see inset). By coupling the two reinforcement rings 218C and 218E, the optical window 220 may be firmly attached and sealed to the support structure 202. Although not depicted, the reinforcement ring 218D may similarly be coupled to an adjacent reinforcement ring disposed in the support structure 202. However, in some embodiments, the optical window 222 may be co-formed with the support structure 202. The two reinforcement rings 218C and 218E may be coupled by clamps 232. The clamps 232 may be formed into one of the reinforcement rings 218C, E, and extend around an outer edge of the other. Alternatively, the two reinforcement rings 218C, E may be coupled by pins inserted into holes or recesses formed in the two reinforcement rings. Of course, other coupling mechanisms may be implemented and are contemplated herein.

Figure 3:
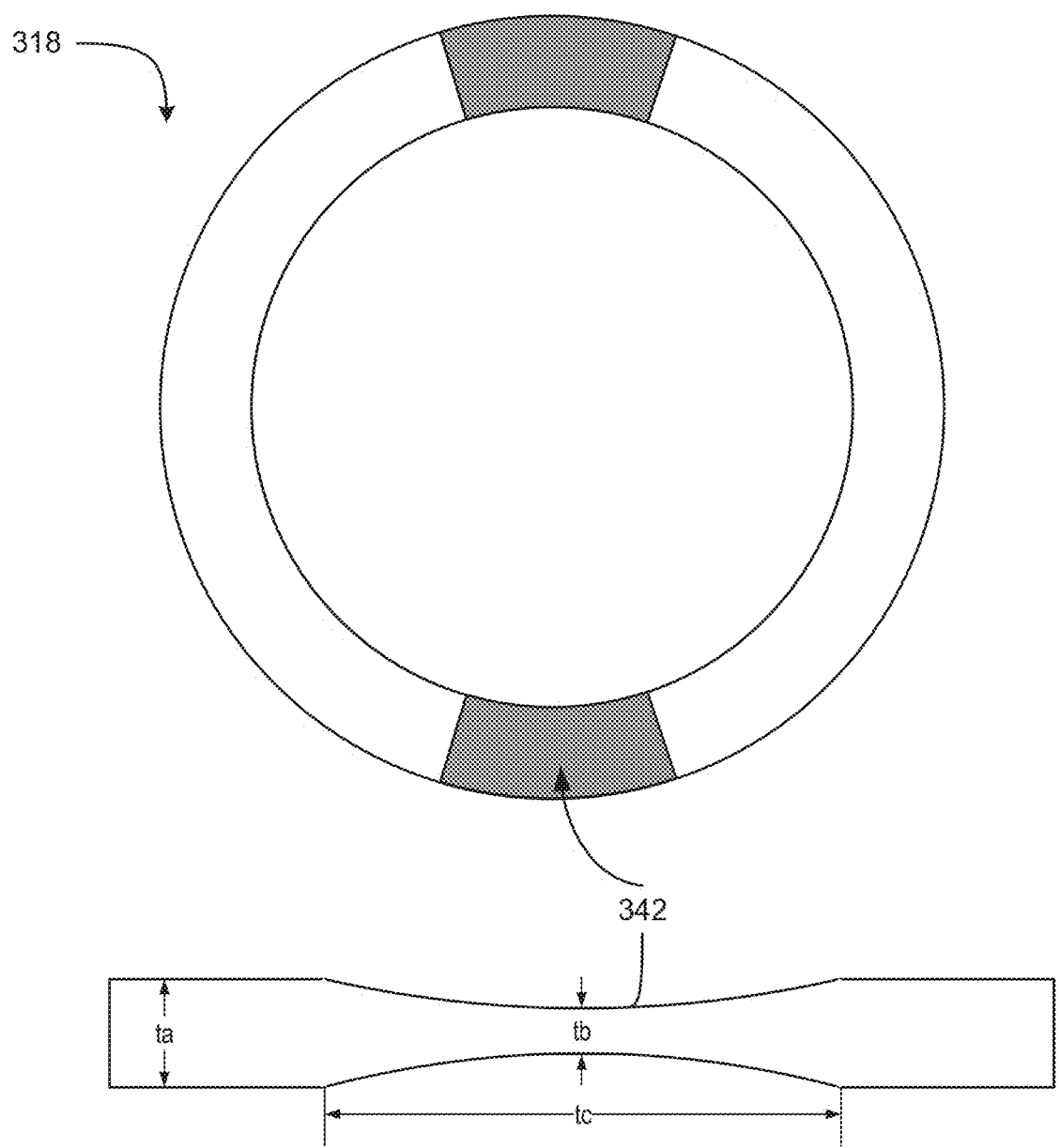
FIG. 3 is an illustrative reinforcement ring in accordance with an embodiment of the present disclosure.

FIG. 3 is an illustrative reinforcement ring 318 in accordance with an embodiment of the present disclosure. The reinforcement ring 318 may be an example of the reinforcement rings 118 and/or 218A through 218E. In the illustrated embodiment, the reinforcement ring 318 may have two folding zones 342 that are thinner than the remainder of the reinforcement ring 318. While only two folding zones 342 are shown, additional folding zones may be included, such as four or six folding zones. The folding zones 342 may be half the thickness of the remainder 340, which may provide areas specific for bending/rolling of the reinforcement ring 318 for the insertion process. In some embodiments, the remainder of the reinforcement ring 318 may provide a sturdy surface for locating control electronics and/or an antenna.

The folding zones 342 may have a thickness tb that, as noted, is thinner than the thickness ta of the rest of the reinforcement ring 318. While tb may be about half of ta in some embodiments, the relative thickness of tb may be adjusted based on a desired bending radius, material choices, and thickness ta. The folding zones 342 may have a radial length tc, which may be adjusted based on the same factors. The length tc of the folding zone may affect the desired bending radius, and may be adjusted in response.

Figure 4:
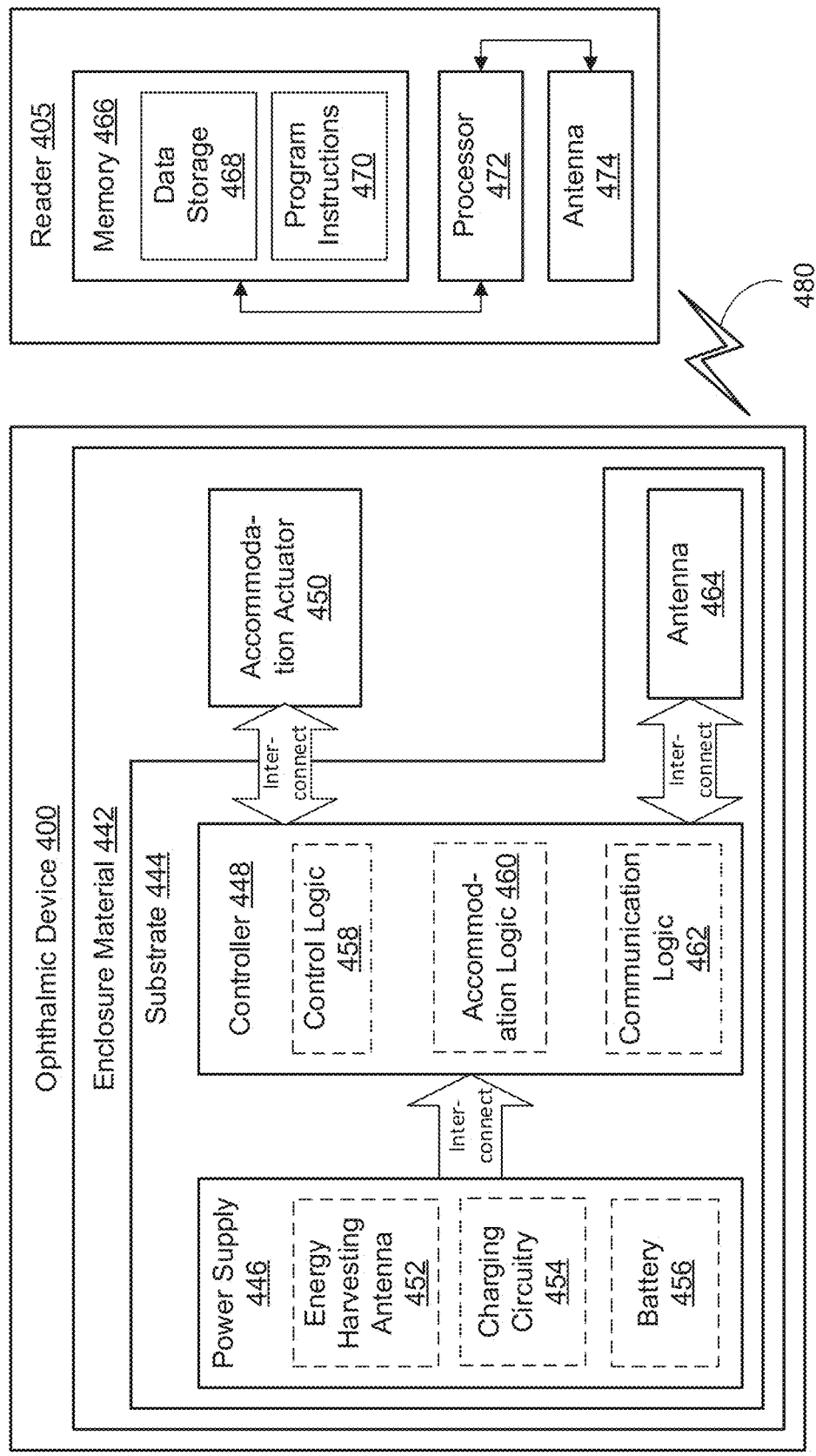
FIG. 4 is a functional block diagram of an ophthalmic device including a hermetic barrier disposed on a conductor in accordance with an embodiment of the present disclosure.

FIG. 4 is a functional block diagram of an ophthalmic device 400 including a hermetic barrier disposed on a conductor in accordance with an embodiment of the present disclosure. Ophthalmic device 400 may be an implantable device, such as an intraocular lens, and may be one example of the IOLs 100 and/or 200. In the depicted embodiment, ophthalmic device 400 includes an enclosure material 442 formed to be implanted into an eye. A substrate 444 is embedded within or surrounded by enclosure material 442 to provide a mounting surface for a power supply 446, a controller 448, an antenna 464, and various interconnects. The substrate 444 and the associated electronics may be one implementation of the control electronics 108 and an associated substrate. In some embodiments, a reinforcement ring may be used as a substrate. In some embodiments, the substrate 444 may be embedded in a support structure, such as the support structure 102, which is embedded in the enclosure material 442. The illustrated embodiment of power supply 446 includes an energy harvesting antenna 452, charging circuitry 454, and a battery 456. The illustrated embodiment of controller 448 includes control logic 458, accommodation logic 460, and communication logic 462. As shown, accommodation actuator 450 is disposed in the enclosure material 442.

Power supply 446 supplies operating voltages to the controller 448 and/or the accommodation actuator 450, which is an example of the dynamic optic 112. Antenna 464 is operated by the controller 448 to communicate information to and/or from ophthalmic device 400. In the illustrated embodiment, antenna 464, controller 448, and power supply 446 are disposed on/in substrate 444, while accommodation actuator 450 is disposed in enclosure material 442, such as in an aperture area of a support structure (not shown) and not in/on substrate 444. However, in other embodiments, the various pieces of circuitry and devices contained in ophthalmic device 400 may be disposed in/on substrate 444 or in enclosure material 442, depending on the specific design of ophthalmic device 400.

Substrate 444 includes one or more surfaces suitable for mounting controller 448, power supply 446, and antenna 464. Substrate 444 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 444 to form circuitry, electrodes, etc. For example, antenna 464 can be formed by depositing a pattern of gold or another conductive material on substrate 444. Similarly, interconnects can be formed by depositing suitable patterns of conductive materials on substrate 444. A combination of resists, masks, and deposition techniques can be employed to pattern materials on substrate 444. Substrate 444 can be a relatively soft material, such as a polymer or another material sufficient to structurally support the circuitry and/or electronics within enclosure material 442 while being flexible enough to being rolled up or folded. Ophthalmic device 400 can alternatively be arranged with a group of unconnected substrates rather than a single substrate 444. For example, controller 448 and power supply 446 can be mounted to one substrate 444, while antenna 464 is mounted to another substrate 444 and the two can be electrically connected via interconnects. Substrate 444 may also be a continuous piece of semiconductor, housing all or some of the aforementioned pieces of device architecture as integrated circuitry.

Substrate 444 can be shaped as a flattened ring with a radial width dimension sufficient to provide a mounting platform for the embedded electronic components. Substrate 444 can have a thickness sufficiently small to allow substrate 444 to be embedded in enclosure material 442 without adversely influencing the profile of ophthalmic device 400. Substrate 444 can have a thickness sufficiently large to provide structural stability suitable for supporting the electronics mounted thereon. For example, substrate 444 can be shaped as a ring with a diameter of about 10 millimeters, a radial width of about 1 millimeter (e.g., an outer radius 1 millimeter larger than an inner radius), and a thickness of about 50 micrometers. In some embodiments, the substrate 444 may encircle at least the optical area associated with the accommodation actuator 450, and may be analogous to the support structures 102 and/or 202. For example, the substrate 444 may be disposed in a peripheral area and in between at least two optical elements, such as optical elements 214 and 216.

Additionally, the power supply 446 may be coupled to the controller 448 via one or more interconnects. Similarly, the controller 448 may be coupled to the accommodation actuator 450 and the antenna 464 via one or more interconnects. The interconnects may be examples of the conductor 116. In some embodiments, the interconnects may be covered by a hermetic barrier structure (not shown) similar to at least the hermetic barrier structure 432.

In the illustrated embodiment, power supply 446 includes a battery 456 to power the various embedded electronics, including controller 448. Battery 456 may be inductively charged by charging circuitry 454 and energy harvesting antenna 452. In one embodiment, antenna 464 and energy harvesting antenna 452 are independent antennae, which serve their respective functions of energy harvesting and communications. In another embodiment, energy harvesting antenna 452 and antenna 464 are the same physical antenna that are time shared for their respective functions of inductive charging and wireless communications with reader 405. Additionally or alternatively, power supply 446 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 454 may include a rectifier/regulator to condition the captured energy for charging battery 456 and/or directly power controller 448. Charging circuitry 454 may also include one or more energy storage devices to mitigate high frequency variations in energy harvesting antenna 452. For example, one or more energy storage devices (e.g., a capacitor, an inductor, etc.) can be connected to function as a low-pass filter.

Controller 448 contains logic to choreograph the operation of the other embedded components. Control logic 458 controls the general operation of ophthalmic device 400, including providing a logical user interface, power control functionality, etc. Accommodation logic 460 includes logic for receiving signals from sensors monitoring the orientation of the eye, determining the current gaze direction or focal distance of the user, and manipulating accommodation actuator 450 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 462 provides communication protocols for wireless communication with reader 405 via antenna 464. In one embodiment, communication logic 462 provides backscatter communication via antenna 464 when in the presence of an electromagnetic field 480 output from reader 405. In one embodiment, communication logic 462 operates as a smart wireless radio-frequency identification ("RFID") tag that modulates the impedance of antenna 464 for backscatter wireless communications. The various logic modules of controller 448 may be implemented in software/firmware executed on a general purpose microprocessor, in hardware (e.g., application specific integrated circuit), or a combination of both.

Ophthalmic device 400 may include various other embedded electronics and logic modules. For example, a light source or pixel array may be included to provide visible feedback to the user. An accelerometer or gyroscope may be included to provide positional, rotational, directional or acceleration feedback information to controller 448.

The illustrated embodiment also includes reader 405 with a processor 472, an antenna 474, and memory 466. Memory 466 in reader 405 includes data storage 468 and program instructions 470. As shown reader 405 may be disposed outside of ophthalmic device 400, but may be placed in its proximity to charge ophthalmic device 400, send instructions to ophthalmic device 400, and/or extract data from ophthalmic device 400. In one embodiment, reader 405 may resemble a conventional contact lens holder that the user places ophthalmic device 400 in at night to charge, extract data, clean the lens, etc.

External reader 405 includes antenna 474 (or group of more than one antenna) to send and receive wireless signals 480 to and from ophthalmic device 400. External reader 405 also includes a computing system with processor 472 in communication with memory 466. Memory 466 is a non-transitory computer-readable medium that can include, without limitation, magnetic disks, optical disks, organic memory, and/or any other volatile (e.g., RAM) or non-volatile (e.g., ROM) storage system readable by the processor 472. Memory 466 can include a data storage 468 to store indications of data, such as data logs (e.g., user logs), program settings (e.g., to adjust behavior of ophthalmic device 400 and/or external reader 405), etc. Memory 466 can also include program instructions 470 for execution by processor 472 to cause the external reader 405 to perform processes specified by the instructions 470. For example, program instructions 470 can cause external reader 405 to provide a user interface that allows for retrieving information communicated from ophthalmic device 400 or allows transmitting information to ophthalmic device 400 to program or otherwise select operational modes of ophthalmic device 400. External reader 405 can also include one or more hardware components for operating antenna 474 to send and receive wireless signals 480 to and from ophthalmic device 400.

External reader 405 can be a smart phone, digital assistant, or other portable computing device with wireless connectivity sufficient to provide the wireless communication link 480. External reader 405 can also be implemented as an antenna module that can be plugged into a portable computing device, such as in an embodiment where the communication link 480 operates at carrier frequencies not commonly employed in portable computing devices. In some instances, external reader 405 is a special-purpose device configured to be worn relatively near a wearer's eye to allow the wireless communication link 480 to operate with a low power budget. For example, the external reader 405 can be integrated in a piece of jewelry such as a necklace, earing, etc. or integrated in an article of clothing worn near the head, such as a hat, headband, etc.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus comprising:
    a support structure defining an opening in which a dynamic optic is disposed;
    first and second optical windows disposed on opposing sides of the support structure and each extending across the opening, wherein the first and second optical windows are distinct elements from the dynamic optic; and
    a reinforcement ring included in the apparatus to strengthen the support structure and the first and second optical windows,
    wherein the reinforcement ring is embedded in the first or second optical window.

2. The apparatus of claim 1, wherein the reinforcement ring is embedded in the first optical window, the apparatus further comprising:
    an additional reinforcement ring embedded in one of the support structure or the second optical window.

3. The apparatus of claim 1, wherein the support structure is annular shaped.

4. The apparatus of claim 3, wherein the reinforcement ring is disposed adjacent an electrode.

5. The apparatus of claim 3, wherein the reinforcement ring is an electrode.

6. The apparatus of claim 1, further comprising a second reinforcement ring disposed in the support structure adjacent to the first optical window, and wherein the reinforcement ring is disposed in the first optical window.

7. The apparatus of claim 6, wherein the reinforcement ring and the second reinforcement ring are coupled together.

8. The apparatus of claim 7, wherein one or more clamps couple the reinforcement ring and the second reinforcement ring.

9. The apparatus of claim 1, wherein the reinforcement ring is formed from a superelastic alloy.

10. The apparatus of claim 9, wherein the super elastic alloy is selected from one of Nitinol, copper-zinc-aluminum, copper-aluminum, copper-aluminum-nickel, and copper-aluminum-beryllium.

11. The apparatus of claim 1, wherein the reinforcement ring is formed from one of polyimide, polyetherimide, polyethylene terephthalate, polyether ether ketone, or combinations thereof.

12. The apparatus of claim 1, wherein the support structure is annular shaped forming an aperture in the opening, and wherein the
    the dynamic optic is arranged in the aperture and coupled to provide dynamic accommodation in response to a control signal.

13. The apparatus of claim 12, further comprising:
    control electronics disposed in or on the support structure and electrically coupled to control the dynamic optic, wherein the control electronics are coupled to the dynamic optic via at least one conductor to provide the control signal.

14. The apparatus of claim 1, further comprising an antenna.

15. The apparatus of claim 14, wherein the antenna is disposed on the reinforcement ring.

16. The apparatus of claim 14, wherein the reinforcement ring is the antenna.

17. An apparatus, comprising:
- a support structure having an aperture defined by a sidewall of the support structure;
- a first optical window extending across the aperture;
- a reinforcement ring included in the first optical window to strengthen the support structure and the first optical window, wherein the reinforcement ring is formed from a shape memory alloy;
- a dynamic optic arranged in the aperture, and coupled to provide dynamic accommodation in response to a control signal; and
- control electronics disposed in or on the support structure and electrically coupled to control the dynamic optic, wherein the control electronics are coupled to the dynamic optic via at least one conductor to provide the control signal.

18. The apparatus of claim 17, wherein the reinforcement ring is disposed adjacent to an electrode disposed in or on the support structure.

19. The apparatus of claim 17, wherein the reinforcement ring is an electrode.

20. The apparatus of claim 17, further comprising a second reinforcement ring disposed in the support structure adjacent to the first optical window.

21. The apparatus of claim 20, wherein the reinforcement ring and the second reinforcement ring are coupled together.

22. The apparatus of claim 17, wherein the shape memory alloy is Nitinol.

23. An intraocular lens comprising:
- a support structure having an aperture;
- a dynamic optic disposed within the aperture of the support structure;
- an electrode surrounding the dynamic optic;
- an antenna disposed in or on the support structure and surrounding the dynamic optic;
- at least one optical window spanning the aperture of the support structure; and
- a reinforcement ring disposed in or on the support structure and surrounding the dynamic optic to strengthen the support structure and the at least one optical window,
- wherein the reinforcement ring is a distinct element from the electrode and the antenna and wherein the reinforcement ring is disposed in direct contact with one of the electrode or the antenna.

24. The intraocular lens of claim 23, wherein the support structure is annular shaped and includes an internal sidewall, and wherein the reinforcement ring is disposed in the internal sidewall.

25. The intraocular lens of claim 23, wherein the antenna or the electrode is disposed directly on the reinforcement ring.

* * * * *